United States Patent
Brown et al.

(10) Patent No.: US 9,421,342 B2
(45) Date of Patent: *Aug. 23, 2016

(54) RANDOMLY INTERRUPTED BREATHING DEVICE

(71) Applicant: Actegy Limited, Berkshire (GB)

(72) Inventors: Roger Leslie Brown, London (GB); David Paul Sumners, Barwick Stock on Tees (GB)

(73) Assignee: Actegy Limited, Berkshire (GB)

( * ) Notice: Subject to any disclaimer, the term of this patent is extended or adjusted under 35 U.S.C. 154(b) by 480 days.

This patent is subject to a terminal disclaimer.

(21) Appl. No.: 13/896,465

(22) Filed: May 17, 2013

(65) Prior Publication Data

US 2013/0319416 A1    Dec. 5, 2013

Related U.S. Application Data

(63) Continuation of application No. 11/845,898, filed on Aug. 28, 2007, now Pat. No. 8,469,029.

(30) Foreign Application Priority Data

Sep. 5, 2006  (GB) .................................. 0617354.6

(51) Int. Cl.
*A61M 16/20* (2006.01)
*A61M 16/06* (2006.01)
(Continued)

(52) U.S. Cl.
CPC ........... *A61M 16/20* (2013.01); *A61M 16/0006* (2014.02); *A61M 16/06* (2013.01);
(Continued)

(58) Field of Classification Search
CPC .......... A61B 5/08; A61B 5/087; A61H 23/00; A61M 15/00; A61M 16/00; A61M 16/0006; A61M 16/0057; A61M 16/0066; A61M 16/0096; A61M 16/0677; A61M 16/161; A61M 16/20; A61M 16/204; A61M 16/205; A61M 2016/0018; A61M 2016/0021; A61M 2016/0039; A61M 2205/125; A61M 2205/3331; A61M 2205/3368; A61M 2205/3569; A61M 2205/3584; A61M 2205/3592; A61M 2205/42; A61M 2205/502; A61M 2205/52; A61M 2205/8206; A61M 2205/8237; A61M 2205/8275; A62B 9/02; A63B 2220/16; A63B 2220/56; A63B 2220/58; A63B 23/00; A63B 23/18; A63B 21/00058; A63B 21/00061; A63B 21/00069; A63B 21/00196; F16K 11/06; F16K 11/076; H03K 5/08; H03K 5/088
USPC ............ 128/200.24, 200.26, 200.27, 200.28, 128/201.25, 201.29, 202.16, 203.24, 128/204.11, 204.18, 204.19, 204.21, 128/204.23, 205.12, 205.22, 205.24, 128/205.27, 207.16

See application file for complete search history.

(56) References Cited

U.S. PATENT DOCUMENTS

| 4,471,773 A | 9/1984 | Bunnell et al. |
| 5,193,529 A | 3/1993 | Labaere |

(Continued)

FOREIGN PATENT DOCUMENTS

| EP | 1103287 A3 | 2/2003 |
| FR | 2744922 A1 | 2/1996 |

(Continued)

OTHER PUBLICATIONS

Djarova et al., "Human Growth Hormone, Cortisol, and Acid-Base Balance Changes After Hyperventilation and Breath-Holding", Int'l J. Sports Med., vol. 7, No. 6, pp. 311-315, 1986.

(Continued)

*Primary Examiner* — Annette Dixon
(74) *Attorney, Agent, or Firm* — Barkume & Associates, P.C.

(57) ABSTRACT

Apparatus for randomly varying the breathing resistance applied to human and animal subjects to improve their performance.

27 Claims, 14 Drawing Sheets

(51) Int. Cl.
*A63B 23/18* (2006.01)
*A63B 21/00* (2006.01)
*A61M 16/00* (2006.01)

(52) U.S. Cl.
CPC ..... *A63B21/00069* (2013.01); *A63B 21/00196* (2013.01); *A63B 23/18* (2013.01); *A63B 2208/14* (2013.01); *A63B 2209/08* (2013.01); *A63B 2225/20* (2013.01); *A63B 2230/40* (2013.01)

(56) References Cited

U.S. PATENT DOCUMENTS

| | | | | |
|---|---|---|---|---|
| 5,249,570 | A * | 10/1993 | Cox | A01K 25/00 128/203.25 |
| 5,567,127 | A * | 10/1996 | Wentz | A47L 7/00 415/119 |
| 6,083,141 | A | 7/2000 | Hougen | |
| 6,158,434 | A * | 12/2000 | Lugtigheid | A61M 16/12 128/204.22 |
| 6,349,724 | B1 * | 2/2002 | Burton | A61M 16/0057 128/204.18 |
| 6,581,596 | B1 * | 6/2003 | Truitt | A61M 16/0006 128/204.18 |
| 6,708,690 | B1 | 3/2004 | Hete et al. | |
| 6,776,159 | B2 | 8/2004 | Pelerossi et al. | |
| 7,413,413 | B2 * | 8/2008 | Schnetzka | F04C 29/06 417/410.1 |
| 8,469,029 | B2 * | 6/2013 | Brown | A63B 21/00196 128/204.18 |
| 2003/0111245 | A1 * | 6/2003 | Haggerty | G06F 1/1632 174/50 |
| 2004/0000310 | A1 | 1/2004 | Wickham et al. | |
| 2004/0212997 | A1 * | 10/2004 | Ballarini | A45B 3/04 362/249.01 |

FOREIGN PATENT DOCUMENTS

| | | |
|---|---|---|
| GB | 2196858 A | 5/1998 |
| GB | 2425488 A | 1/2006 |
| WO | WO03077823 A1 | 9/2003 |
| WO | 2005006980 A1 | 1/2005 |

OTHER PUBLICATIONS

Bosco et al., "Hormonal Responses to Whole-Body Vibration in Men", Eur. J. Appl. Physiol. (2000) 81:449-454.

* cited by examiner

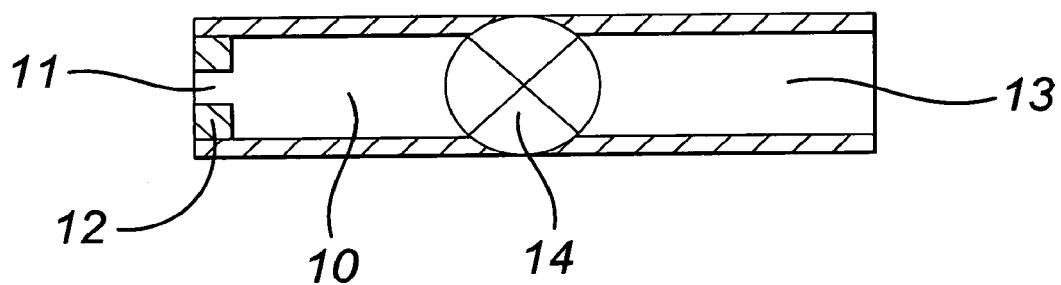
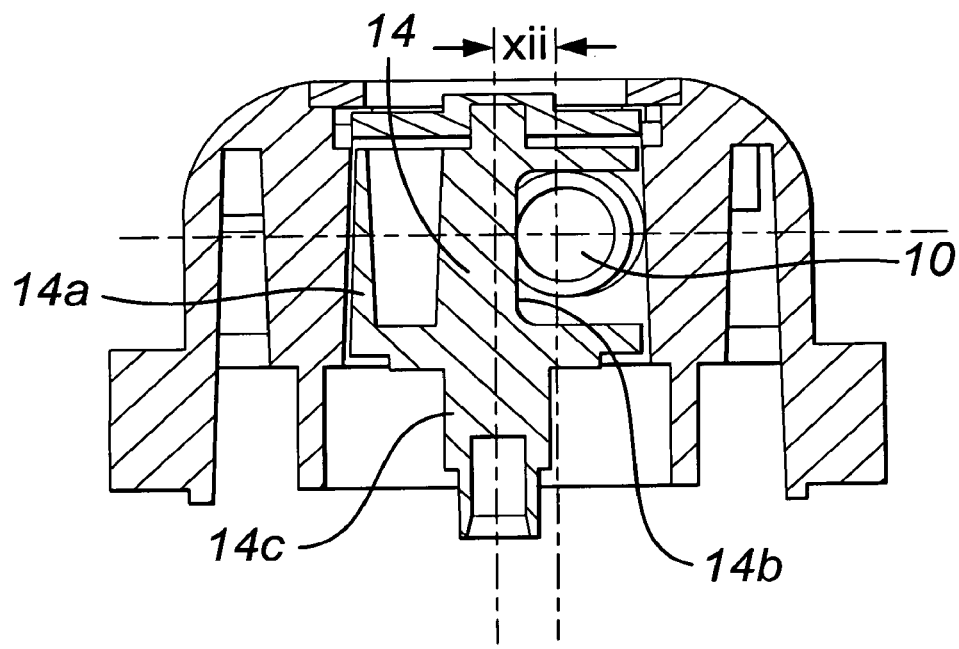

LEGEND
117  mouthpiece
118  inlet
121  conduit
130  rotary valve
140  rotary valve
131  valve
141  valve LEGEND
217 mouthpiece
218 inlet
218a inlet
221 conduit
221a conduit
230 valve
231 motor
240 valve
241 motor LEGEND
100 conduit
101 inlet
102 mouthpiece
103 sensor
104 sensor
105 inlet sensor
106 data processor
107 valve LEGEND
100 conduit
101 inlet
102 mouthpiece
103 sensor
104 sensor
105 inlet sensor
106 data processor
107 valve
108 feedback facility LEGEND
| | |
|---|---|
| 100 | conduit |
| 101 | inlet |
| 102 | mouthpiece |
| 103 | sensor |
| 104 | sensor |
| 105 | inlet sensor |
| 106 | data processor |
| 107 | valve |
| 108 | feedback facility |
| 109 | warning device |
| 110 | storage device |
| 111 | control system |
| 112 | cable |
| 113 | wireless link |

LEGEND
300  plug
301  conduit

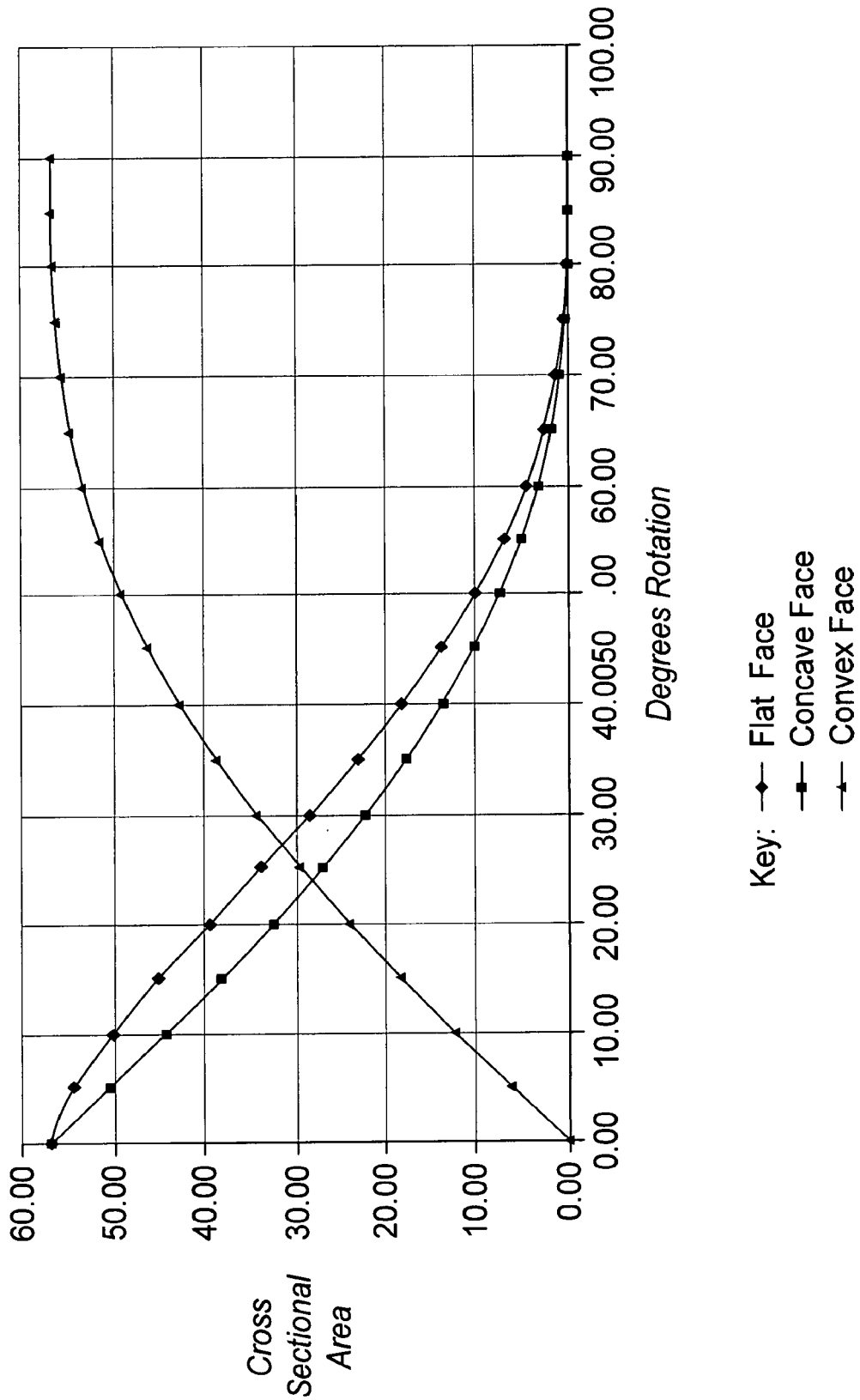

RANDOMLY INTERRUPTED BREATHING DEVICE

CROSS-REFERENCE TO RELATED APPLICATION

This application is related to our co-pending U.S. application Ser. No. 11/845,916, entitled PORTABLE BREATHING DEVICE, which was filed on Aug. 28, 2007, which issued as U.S. Pat. No. 8,360,061 on Jan. 29, 2013 and which is assigned to the same assignee as the present application.

BACKGROUND TO THE INVENTION

The present invention relates to a portable breathing device for providing resistance and intra-trachea bronchial percussion on breathing in and breathing out to increase pulmonary efficiency while improving cilial movement which assists mobilisation of intrabronchial mucous or secretions within the lung. It can be used for increasing breathing efficiency and for training athletes and also in the treatment of medical conditions related to weak breathing.

Patent Application WO 03/077823 discloses a breathing device having an air flow interruption means connected to the breathing means, which causes a regular periodic interruption to air flowing through the interruption means to the user.

U.S. Pat. No. 6,083,141 discloses a breathing device which incorporates a pair of rotating cylinders which interrupt the flow of air to a user of the device.

In these breathing devices there is a mouthpiece which can fit over the mouth and/or nose of a user so that a user breathes through the mouthpiece. This mouthpiece is preferably connected to the interruption means, e.g. by a conduit, or is directly attached to the interruption means. The interruption means is normally a valve and produces regular periodic interruptions to the flow of air reaching the mouthpiece being breathed by a user.

In these devices the frequency of opening and closing the valve is set when the device is turned on and, although the frequency can be varied each time it is used, there is no means of varying the frequency of the opening and closing of the valve whilst the device is being operated.

For training athletes and animals, we have found users can become accustomed to regular interruption of their breathing which can prevent further improvement.

We have now devised an improved method of improving breathing performance.

SUMMARY OF THE INVENTION

According to the invention there is provided a breathing device which comprises:
an air inlet;
an air outlet through which a user breathes;
a conduit connecting the air inlet and outlet;
an air flow interruption means positioned in the conduit so that air entering through the inlet and inhaled by the user can be interrupted by the interruption means; and in which device there are means to vary the frequency of interruption of the flow of air through the conduit.

The device can be used for training purposes such as for an athlete or sportsperson or anyone who wants to improve their breathing. It is well known that improving the breathing of a person can increase their lung capacity and the rate of oxygenation of their muscles, which will result in improved performance. This applies similarly to animals including, of course, racehorses and racing dogs.

The invention also provides a method of training by controlling the breathing by interrupting the inhalation and exhalation of the person or animal being trained at a frequency which varies preferably during use.

Preferably the frequency can be varied randomly.

The interruption means may be a valve mechanism, such as a reed or other oscillating valve system, with the air passing through the valve mechanism being interrupted by a mechanically or electrically controlled valve mechanism.

The frequency of the interruptions to the flow of air is preferably in the range of 5 to 100 Hz, for example 10 to 50 Hz, typically 20 Hz. This means that the flow of air through the interruption means is interrupted at this frequency. It has been discovered that the muscles involved in different regions of the respiratory system are strengthened by different interruption frequencies. Typically the diaphragm may be strengthened the more by an interruption cycle of the order of 5 Hz while for upper respiratory areas 20 Hz to 30 Hz may be the more appropriate. Variability in the interruption rate may accordingly be desirable. This can be obtained by interchangeability of the valves or variability of the speed of operation. Random variation can enhance the strengthening of any of the muscles in the respiratory system.

The air outlet can incorporate a mouthpiece which can fit over the mouth and/or nose of a user so that a user breathes through the mouthpiece and this mouthpiece is connected to the valve in the conduit. The mouthpiece may be detachable so that the user may use different forms thereof, or to suit different users, or for cleaning or maintenance (replacement) purposes.

A preferred valve is a motor driven rotary valve and the frequency of the interruptions to the airflow is controlled by the speed of rotation of the motor. There is preferably a control system which randomly changes the speed of rotation of the motor; such systems are commercially available.

A suitable valve is a rotary valve comprising:
a housing containing a fluid flow path with a central axis;
a plug having a sealing face cooperating with a valve seat in said housing in the closed position to block the fluid flow path; and
a support shaft arranged to carry said plug and being rotatable on an axis which is normal to and spaced from the axis of said valve seat and located outside of the flow path so that rotation of the said shaft moves said plug relative to said housing.

The axis of the plug need not be outside the flow path, but preferably the bearings and shape of the port do not occlude the fluid path. The plug axis may located at an offset which may also be arranged to be adjusted for different effects.

The distance between the axis of the support shaft of the plug means and axis of the fluid flow path is herein called "the offset".

In one arrangement, when the closed or sealing face of the plug is presented in the bore, flow is totally occluded whilst a 180 degrees rotation of the rotary valve will present a completely open aperture allowing full flow through the valve assembly without obstruction, due to the operating mechanism of the valve. The plug preferably has a plane face and, in the open position, this plane is contiguous with the side of the fluid flow path for smooth flow down the fluid flow path.

The plug means is preferably substantially cylindrical or spherical and has a radius larger than the diameter of the flow path; however the cross-section of the plug may deviate from strict circularity.

If the offset and plug diameter are increased while the width of the sealing face of the plug is maintained as equivalent to the bore diameter, a shorter angular opening period is provided for any given rotational speed, which can prove useful if a specific mechanical timing/angular relationship is desired between the valve assembly and the drive mechanism rotating the plug to operate the valve.

A further increase in the plug diameter and its locating bore can provide a closure seat in the flow-bore for even better sealing characteristics due to the overlap of position with a small overlap at the edges of the plug and the housing to ensure good sealing in this position.

By introducing variations in the relationship between the width of the sealing face of the plug, port diameter and valve offset, a variety of different conditions may be created to suit the specific application requirement.

The valve offset, diameter and position provide for good sealing when closed, zero flow occlusion when open, and the ability to use a motor-gearbox speed reduction that is half that which is otherwise required with an on-axis rotary valve.

By presenting the sealing face of the plug in the flow path once in each revolution, motor speeds are doubled for any given flow pulse rate when compared to conventional on-axis designs which close the valve twice in each revolution; this causes less low-speed motor torque problems.

Another type of valve comprises a solenoid driven diaphragm placed in the air flow path driven by an electronic pulse the frequency of which can be varied randomly by use of a software or firmware program or electronic hardware circuit to provide a method of opening and closure of the diaphragm and thus provide a constantly changing or set of periodically changing occlusions. In this instance, as in others described herein, the facility of variable frequency may be a feature additional to the provision of non-variability.

Another type of valve is a diaphragm or mechanical port which may be opened and closed by action of a piezo actuator device which is driven by an electronic pulse which frequency can be varied randomly by use of a software or firmware program or electronic hardware circuit to provide a method of opening and closure of the diaphragm and thus provide a constantly changing or set of periodically changing occlusions.

Another way of accomplishing varying valve operation is to employ two or more motors, each driving its own valve. These may be in series or parallel. One valve may be at a constant speed and the other varying or both may vary at different rates. Holding one frequency constant, by for example using a fixed DC drive voltage, and sweeping a second motor control voltage gives a pulse sequence with a huge range of harmonics.

By randomly varying the frequency of the air interruption, improved training results are obtained.

In yet another way of accomplishing varying breathing interruption is to employ a valve comprising two discs, at least one of which can be rotated relative to the other, with one of the discs having at least one void therethrough and the other having a plurality of voids therethough, the discs being positioned in the air flow so that, as at least one of the discs rotates relative to the other disc; the voids in the two discs are periodically coincident so as to form a continuous air flow passage. Interchangeability of at least one of the discs can enable both non-variability and different variabilities in the device.

In addition to a rotating, oscillating or other pulse inducing valve, the main fluid bore diameter may be selected to provide a small background resistance level conducive to the described training effects and upon which the pulsed resistance is superimposed.

The level of background resistance may be varied by a variety of valve arrangements, including a rotary cut-off valve, a disc valve with different selectable apertures, a variable position diaphragm valve, a needle valve, or fixed smaller-bore (relative to main fluid flow bore size) inserted plug. This plug may be manufactured from an elastomeric material dimensioned such that a deformable outer profile can grip the internal walls of the main fluid flow. So that it may be easily inserted and retained, the small bore plug may be supplied with a variety of different internal bore sizes to set different background resistance values as required.

The device can be used for training of athletes for which purpose the device may be adapted to be worn or otherwise carried on the person whilst exercising, e.g. on a treadmill, rowing machine or other machine or running on an athletics track. It can be quite compact, having dimensions of the order of 10 cm by 8 cm by 4 cm.

Usually the motor means is a rotary motor powered by a battery, which may be a rechargeable battery. Mains power may alternatively be used. The motor means may in another embodiment be a hand driven clockwork motor, or a hand drive may be incorporated to charge a battery for a battery driven motor. In yet another embodiment the motor means is a breath driven rotary vane, the vane carrying a magnet which, in co-operation with a static magnet mounted in the device, provides the valve by virtue of the user breathing alternately with and against the magnetic attraction of the two magnets. Any of these three devices may be constructed as integral units, that is to say without a detachable head.

In addition, the device can provide diaphragm muscle toning and enhancement induced by working the muscles such as those used for inspiration and exhalation against both the fixed resistance and superimposed pulsed occlusion provided by the valve and fitted nose restrictor and chosen bore diameter.

Taking deep breaths while performing little physical movement causes a superfluous amount of oxygen to be made available. Because the large muscular tissue is not consuming the oxygen, an increased oxygen supply is made available for many other body systems, such as the brain and the heart.

Forcible and prolonged inspiration and expiration causes a greater expansion and collapse of the air vesicles (alveoli), especially those deep in the lung tissue. By providing resistance to inspiration and expiration, pulmonary muscles are strengthened and developed, thereby allowing a freer and greater exchange of oxygen and carbon dioxide. Persons suffering from lung ailments, healthy persons, and athletes can all improve their pulmonary efficiency through forcible and prolonged inspiration and expiration against resistance.

Randomly varying the frequency of the resistance to inspiration and expiration enhances these effects.

The device may incorporate means for providing the user and or his trainer with performance information, the means perhaps including data gathering sensors, storage and data processing devices and a display monitor.

Studies have demonstrated that vibration stimulation and breathing maneuvers can give a five-fold increase in generalised neuroendocrine response (Djarova et al 1986 and Bosco et al 2000). Devices in accordance with the present invention will cause a change in the release of hormones cortisol and growth hormone and accordingly result performance gains in strength, sprint and power.

BRIEF DESCRIPTION OF THE DRAWINGS

A randomly interrupted breathing device in accordance with the invention will now be described by way of example with reference to the accompanying drawings, in which:

FIG. 1 shows the arrangement of a valve within a conduit with inlet and outlet;

FIG. 2 shows a vertical cross section of a rotary valve configuration;

FIG. 11 is a graph of the effects of varying the form of the face of the valve plug;

DETAILED DESCRIPTION OF SPECIFIC EMBODIMENTS

Figure 3:
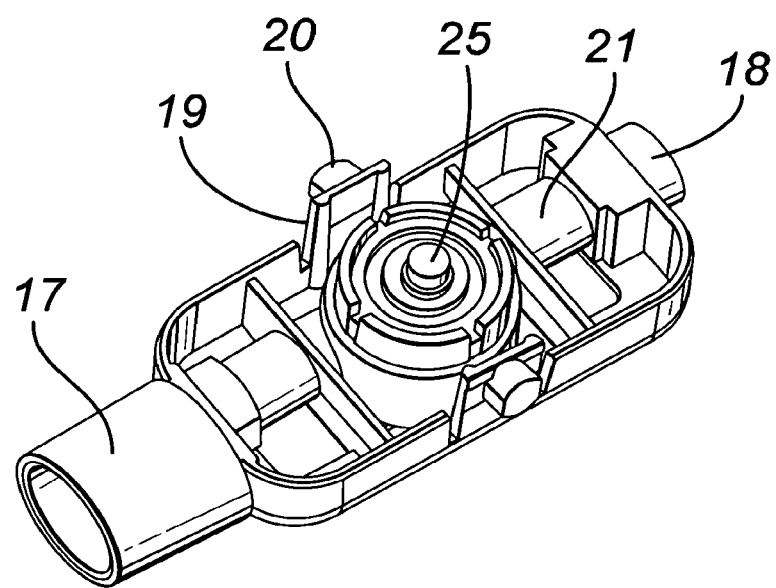
FIG. 3 shows a detachable head device incorporating a rotary valve configuration.

Referring to FIG. 1 there is a fluid flow conduit 10 provided at an inlet 11 end thereof with a restrictor 12 to provide a background breathing resistance when in use and having a mouthpiece end 13. A valve 14 is placed in series in the conduit 10 to provide a pulsed resistance. A control circuit device, not shown, controls the frequency of operation of the valve and is capable of randomly changing the timing of the valve closure. Vibration frequencies between 5 Hz and 100 Hz have been found to provide best results in terms of beneficial lung and diaphragm development to improve oxygen uptake and waste gas removal in human subjects.

The valve 14 is shown in greater detail in FIG. 2 which depicts the valve in a detachable head device, the complete device being illustrated in FIG. 3 and described in co-pending UK patent application 0617349.6 (corresponding to U.S. application Ser. No. 11/845,916, entitled PORTABLE BREATHING DEVICE, filed on even date), the specification of which is incorporated by reference herein. In particular, FIG. 3 illustrates a mouthpiece 17 and an inlet 18, linked by a conduit 21, through which a user can breathe. Flexible flaps 19 carry lugs 20 for a snap fit. Also shown is a drive shaft 25. There is a valve body with a closed face 14a and a relieved face 14b supported on a shaft 14c and offset and normal to the conduit axis by a distance (xii).

Figure 4:
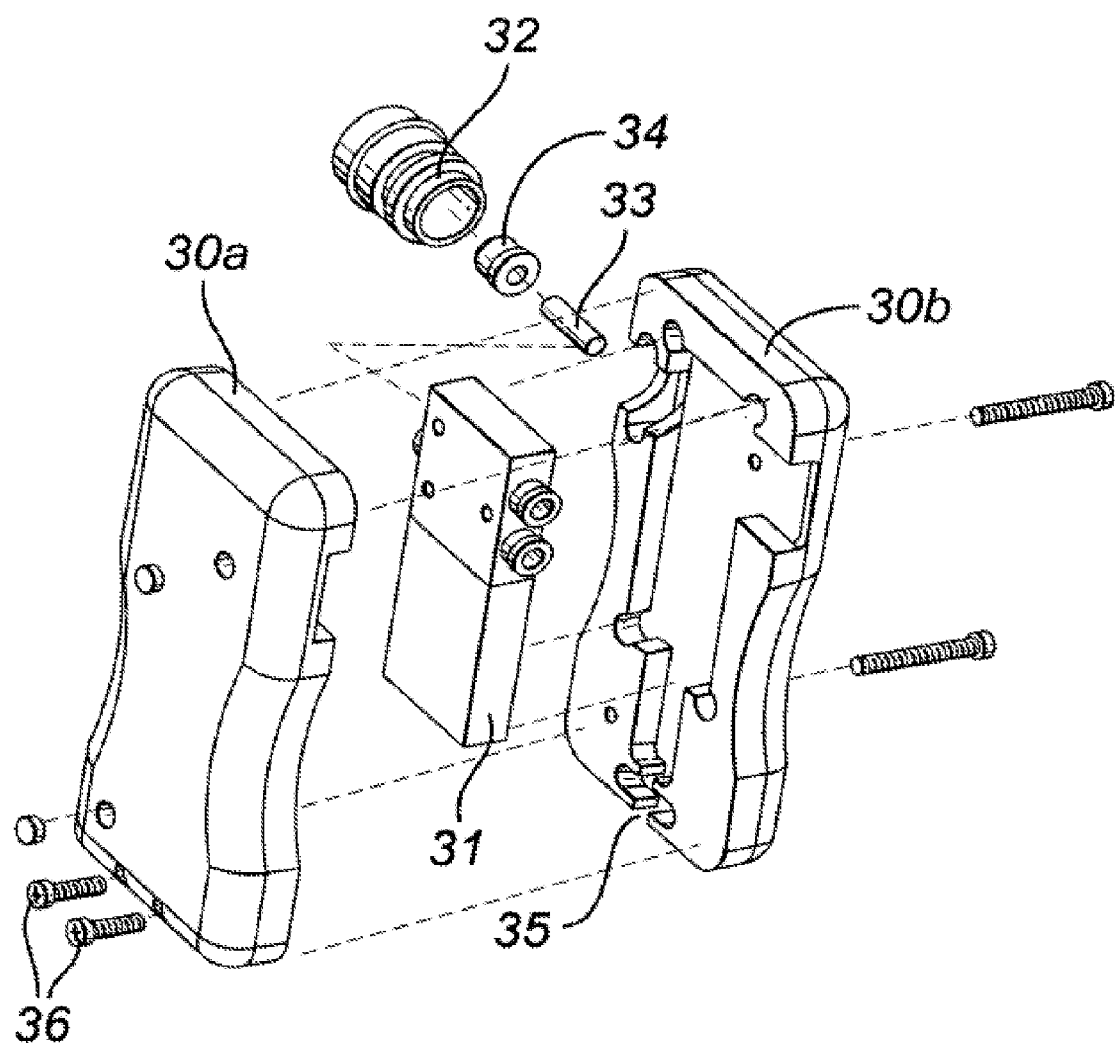
FIG. 4 shows an exploded view of a diaphragm solenoid valve controlled random vibration handset.

The alternative embodiment illustrated in FIG. 4 comprises a handset consisting of two body halves 30a, 30b which retain a solenoid diaphragm valve 31. The valve is connected to a mouthpiece 32 via a short tube 33 and a push-fit union 34. Two screws clamp the body halves 30a, 30b together. Control and power cables (not shown) exit from the solenoid valve through an aperture 35 in the lower sections of the body halves which are strain relieved by clamps secured by fasteners 36. An external power source provides a series of random pulses to the solenoid valve which opens and closes an internal diaphragm superposed in the fluid flow path. A user breathing through the mouthpiece may inhale or exhale and through the action of the small tube 33 experience a resistance to breathing. In addition to this fixed resistance, the random opening and closing of the valve provides a further pulsed restriction in fluid flow that provides a random addition load during the inhale/exhale breathing cycle.

Figure 5:
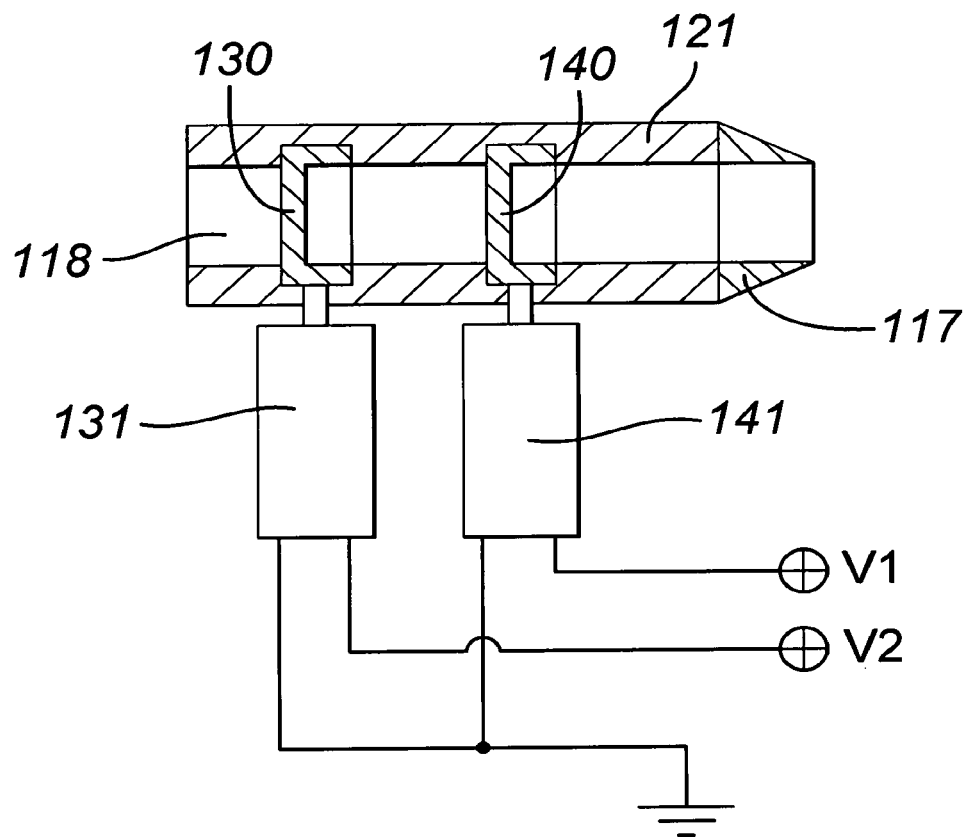
FIG. 5 is a schematic part view of a double motor device with valves in series.

The alternative embodiment illustrated in FIG. 5 has a mouthpiece 117 and an inlet 118 linked by a conduit 121. Across the conduit are two rotary valves 130, 140 in series. The valves are driven by motors 131, 141 respectively. The motor 131 is arranged to operate at constant speed while the motor 141 is arranged to operate at a constantly varying speed. The valves 131, 141 are constructed to occlude airflow for a very small arc of their rotation to arrive at an acceptable base flow occlusion. By this arrangement a considerable variation of occlusion rate is obtained.

Figure 6:
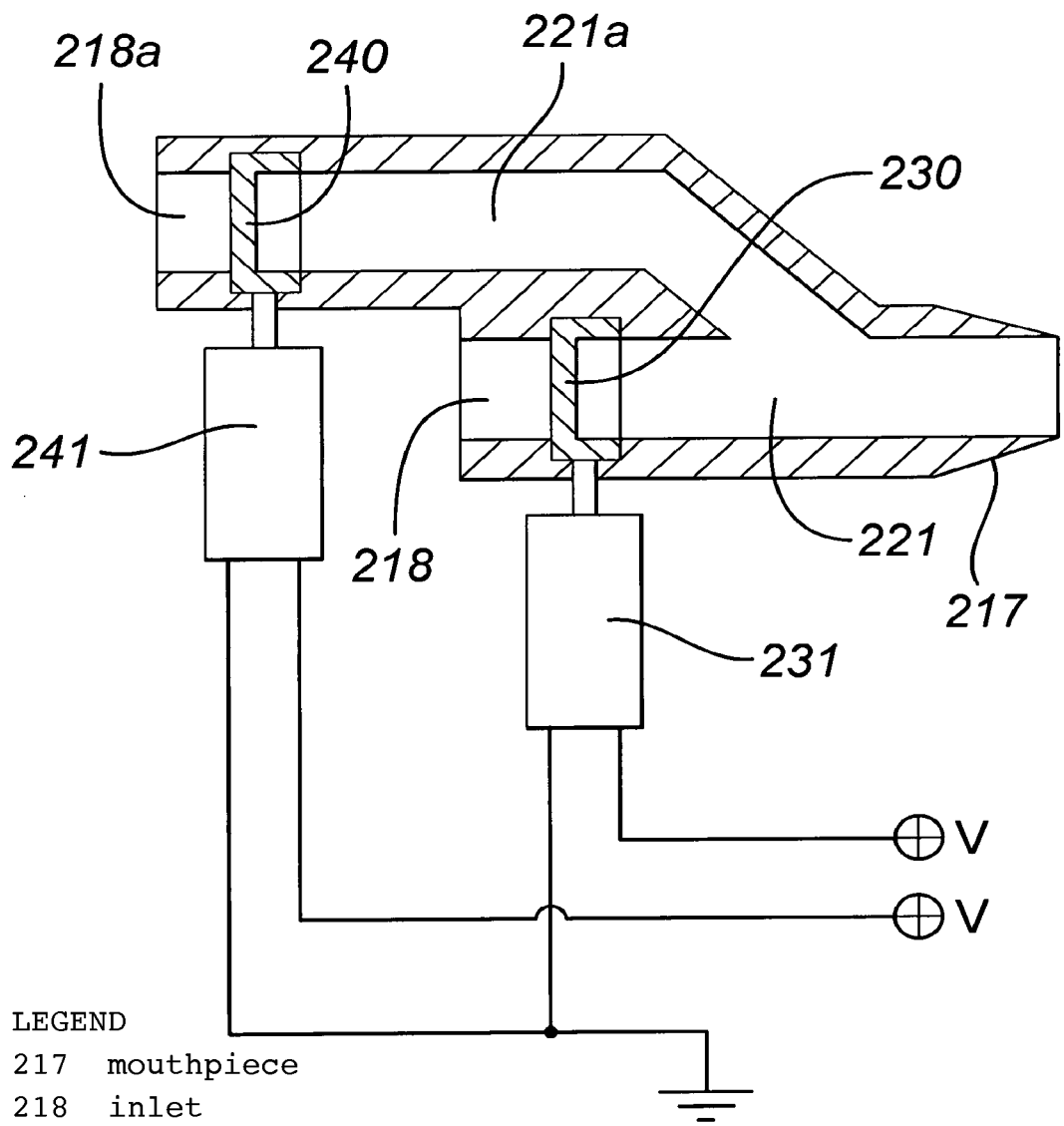
FIG. 6 is a schematic part view of a double motor device with valves in parallel.

The alternative embodiment illustrated in FIG. 6 has a mouthpiece 217 with two associated inlets 218, 218a linked by parallel conduits 221, 221a. Across each conduit 221, 221a is a valve 230, 240 driven by motors 231, 241 respectively. The motor 231 is arranged to operate at constant speed while the motor 241 is arranged to operate at a constantly varying speed.

The motors 131, 141, 231, 241 are conventional DC brush motors and gearboxes permit the valves to rotate at speeds considerably lower than the motors. Stepper motors could be employed instead.

Figure 7:
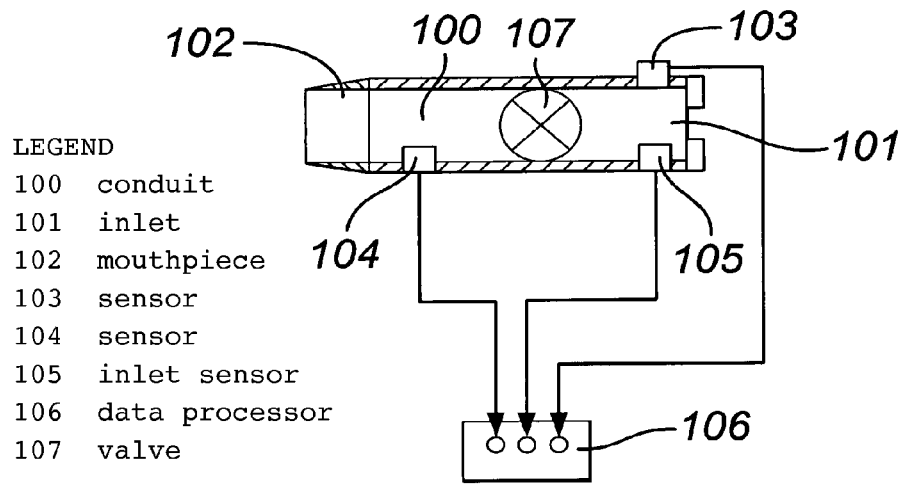
FIG. 7 is a block diagram of a basic monitoring sensor facility.

The device incorporates means for monitoring and analysing a user's performance. A simple such means is illustrated in FIG. 7 which shows a conduit 100 having an inlet 101, a mouthpiece 102 and a valve 107. These correspond to the conduit 10, inlet 11, mouthpiece 13 and valve 14 described above with reference to FIGS. 1 to 6. Exterior to the conduit is an ambient sensor 103 of temperature and pressure. Inside the conduit 100, inboard of the mouthpiece 102, is a "user side" sensor 104 of temperature and pressure. Inside the conduit 100, just inboard of the inlet 101, is an inlet sensor 105 of temperature and pressure. The three sensors are connected to a data processor 106. The sensors 103, 104, 105 may also detect relative humidity.

Figure 8:
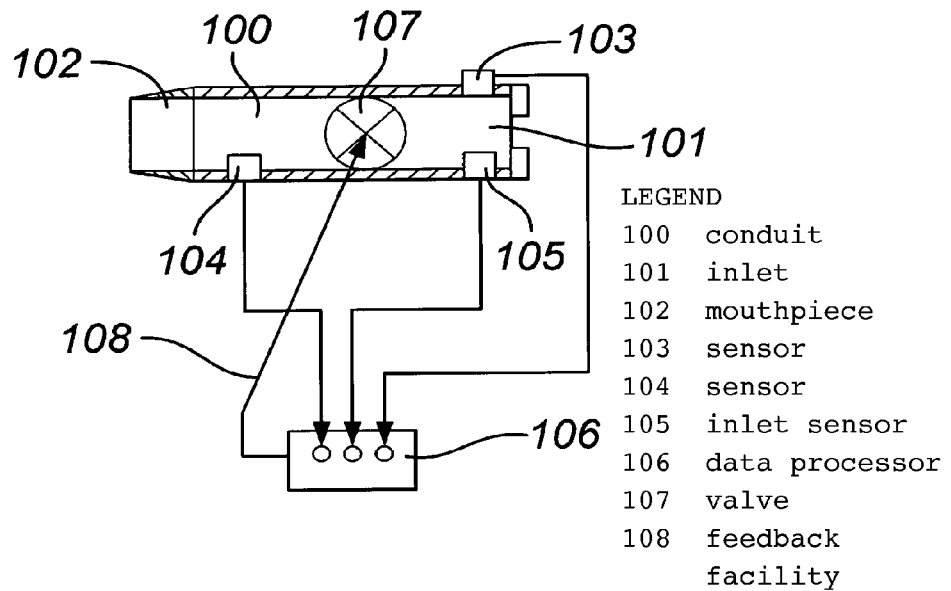
FIG. 8 is a block diagram of a monitoring sensor facility incorporating feedback.

FIG. 8 illustrates means such as that described above with reference to FIG. 7 but incorporating a feedback facility 108.

Figure 9:
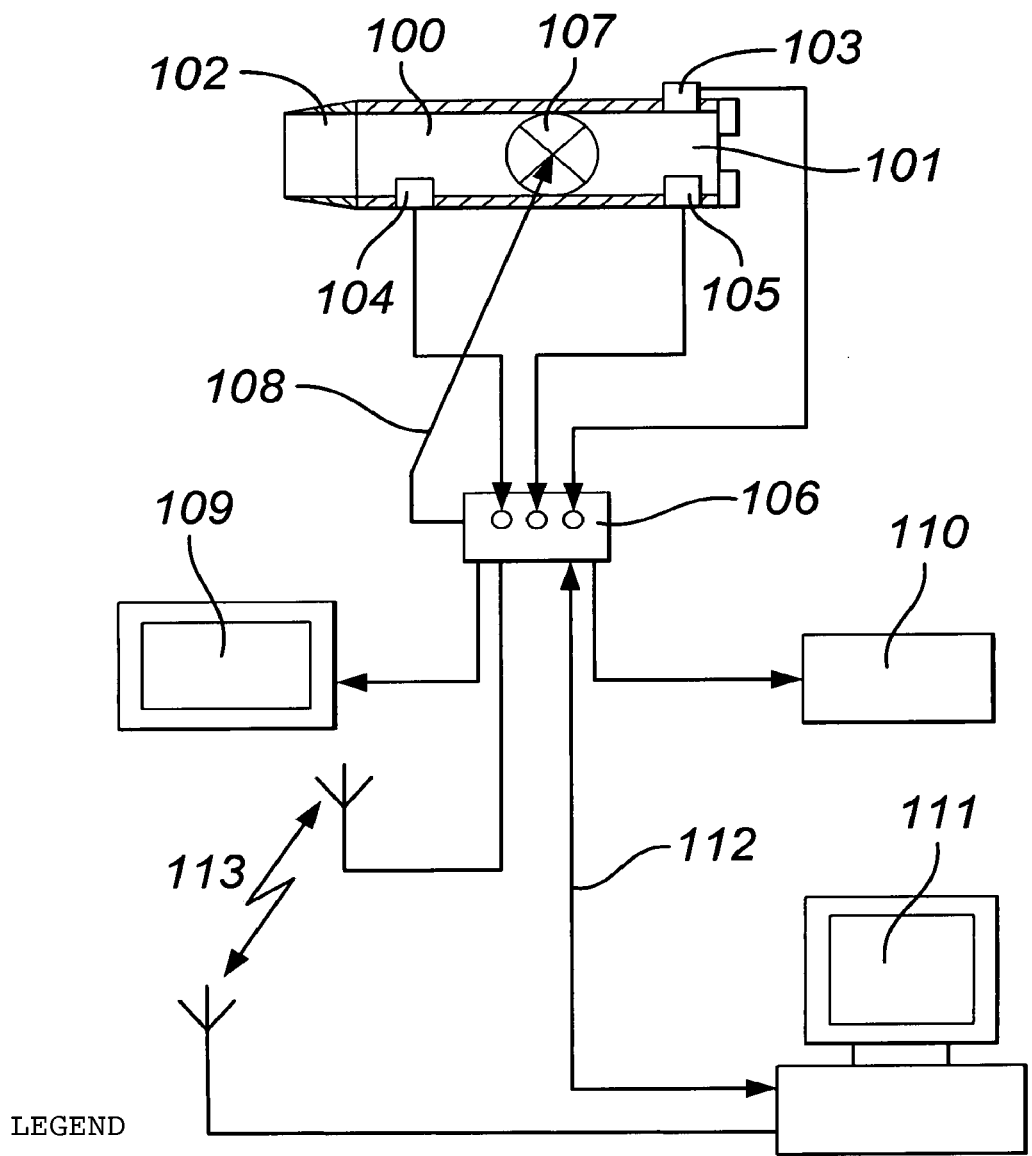
FIG. 9 is a block diagram of a complete monitoring facility.

FIG. 9 illustrates a number of different ways in which output from the data processor 106 can be utilised. An on-board display or warning device 109 provides real time performance information to the user, his medical adviser or his trainer. An on-board data storage device 110 stores performance data for recordal and subsequent analysis. A remote data storage, processing, viewing management and control system 111 is associated with the data processor 106 either via cable 112 or wireless (radio, infra-red, blue tooth) link 113.

Figure 10A:
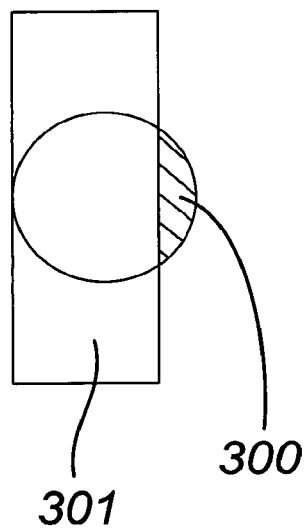
FIGS. 10a, 10b, 10c illustrate valve plugs with differing chords.
Figure 10B:
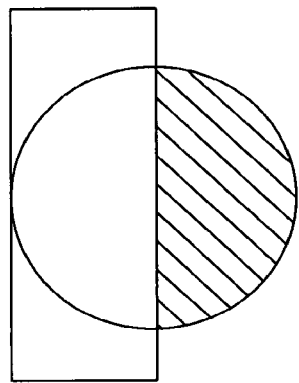
Figure 10C:
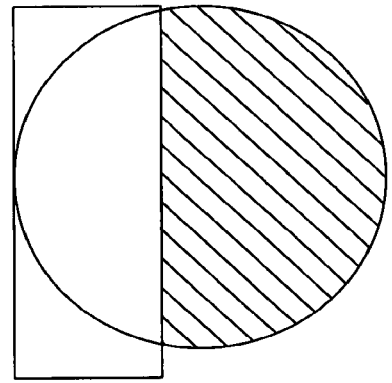

FIGS. 10a, 10b, 10c illustrate schematically valve plugs with different degrees of "cut-away". In FIG. 10a, most of the valve is "cut away" and the axis of rotation of the plug 300 lies within the boundaries of the conduit 301. This construction is produced by having a base to the plug, not shown, disposed beneath the conduit and associated with a drive shaft. Its effect is to produce a large valve opening time in relation to closed time, per revolution. In FIG. 10b the plug axis is tangential to the conduit boundary, approximately half the cylinder forming the valve is "cut away" and valve open and closed times per revolution are approximately equal. In FIG. 10c the plug axis is outside the conduit and less than half the cylinder forming the valve is "cut away". In this case during each revolution the valve is closed for longer than it is open.

Of course the face of the valve does not have to be planar and some modification of the airflow waveform can be obtained by varying it. FIG. 11 compares the effects of a face which is somewhat concave or somewhat convex compared to one which is planar. The planar face valve defines a flow variation which is substantially sinusoidal. A concave face generates a shallower rate of area presentation while a concave face will cause an earlier start to the cut-off and a gentler rate of opening near to maximum.

Figure 12:
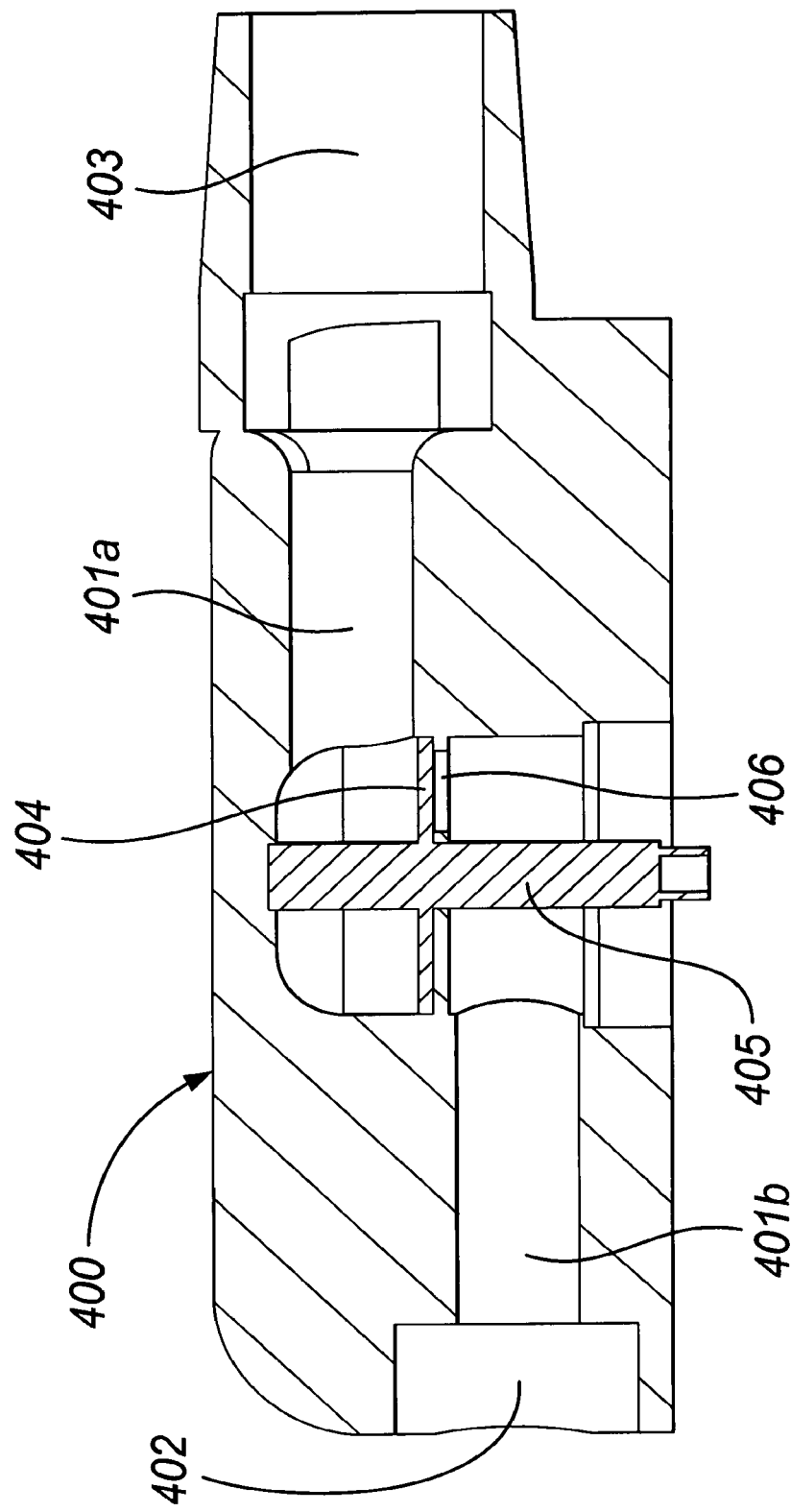
FIG. 12 is a schematic side section of an alternative head.
Figure 13:
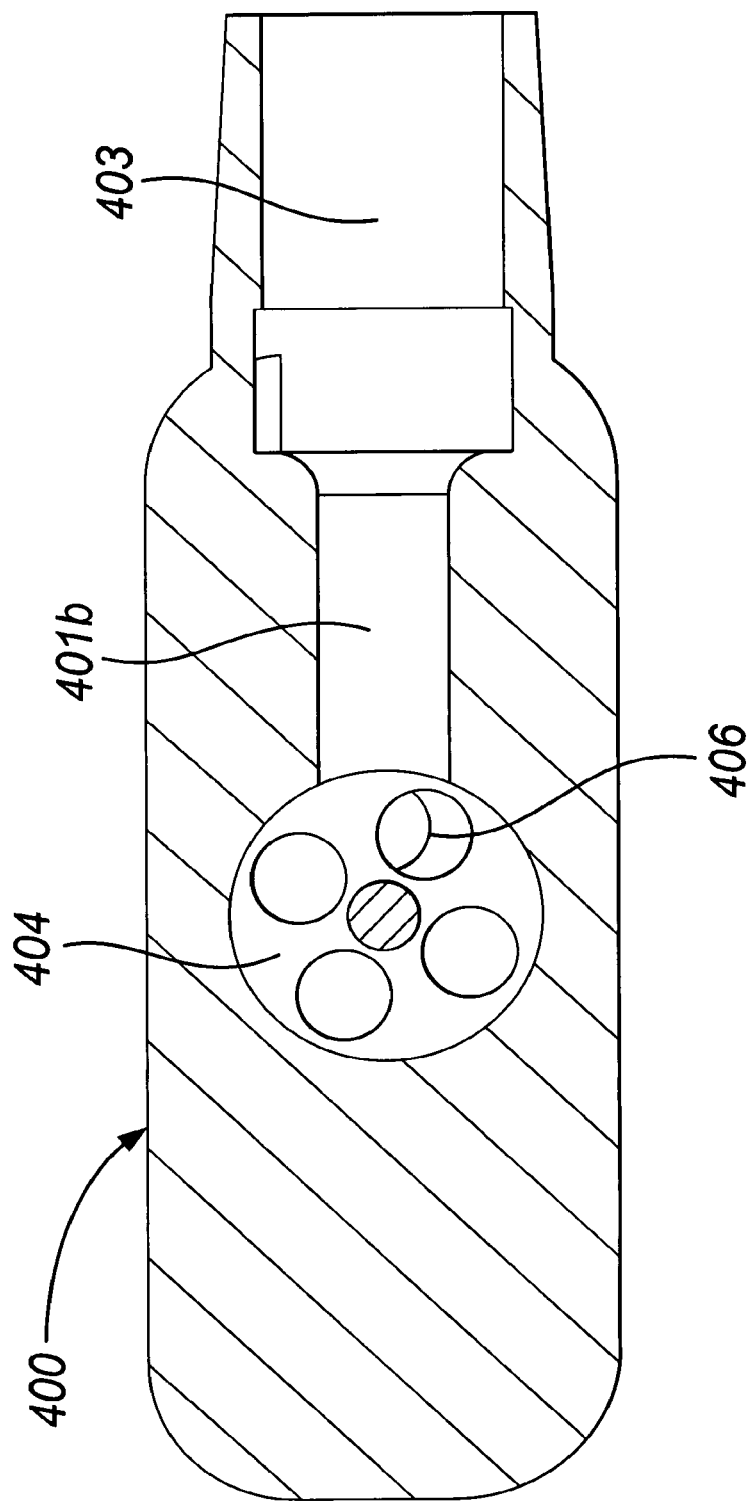
FIG. 13 is a schematic plan section of the alternative head illustrated in FIG. 12.

Another embodiment of the device, a disc valve version, is illustrated in FIGS. 12 and 13. The head 400 defines a conduit in two parts 401a, 401b having an inlet 402 and a mouthpiece 403. The axes of the two parts of the conduit are offset and parallel. Between them is sited a disc valve 404 mounted on a drive shaft 405 and a co-operating valve base plate 406. As shown the valve 404 and the base plate 406 are irregularly foraminous. A variety of forms of perforation of the valve 404 and the plate 406 are possible. Different shapes of the cut away and the holes (or slots) will vary the airflow wave form. Thus an interchangeable set of discs may be provided with one apparatus, including a disc in which the perforations are regularly spaced or even one having the one perforation. In this way the device can progressively strengthen muscles throughout the respiratory system.

Alternative embodiments of the invention incorporate an adjustable speed control. In one of these this adjustment is arranged for control by the user; in another, once initiated it is arranged for periodic speed variation and in another for random speed variation. These facilities are particularly valuable in training athletes and animals used in sport.

Normally in the hand-held device envisaged the power to drive the motor is from a battery incorporated in the base of the device, which may be rechargeable. Mains power may alternatively be employed. In another alternative a power storage unit is employed whence the electricity is derived by turning a handle manually.

Figure 14:
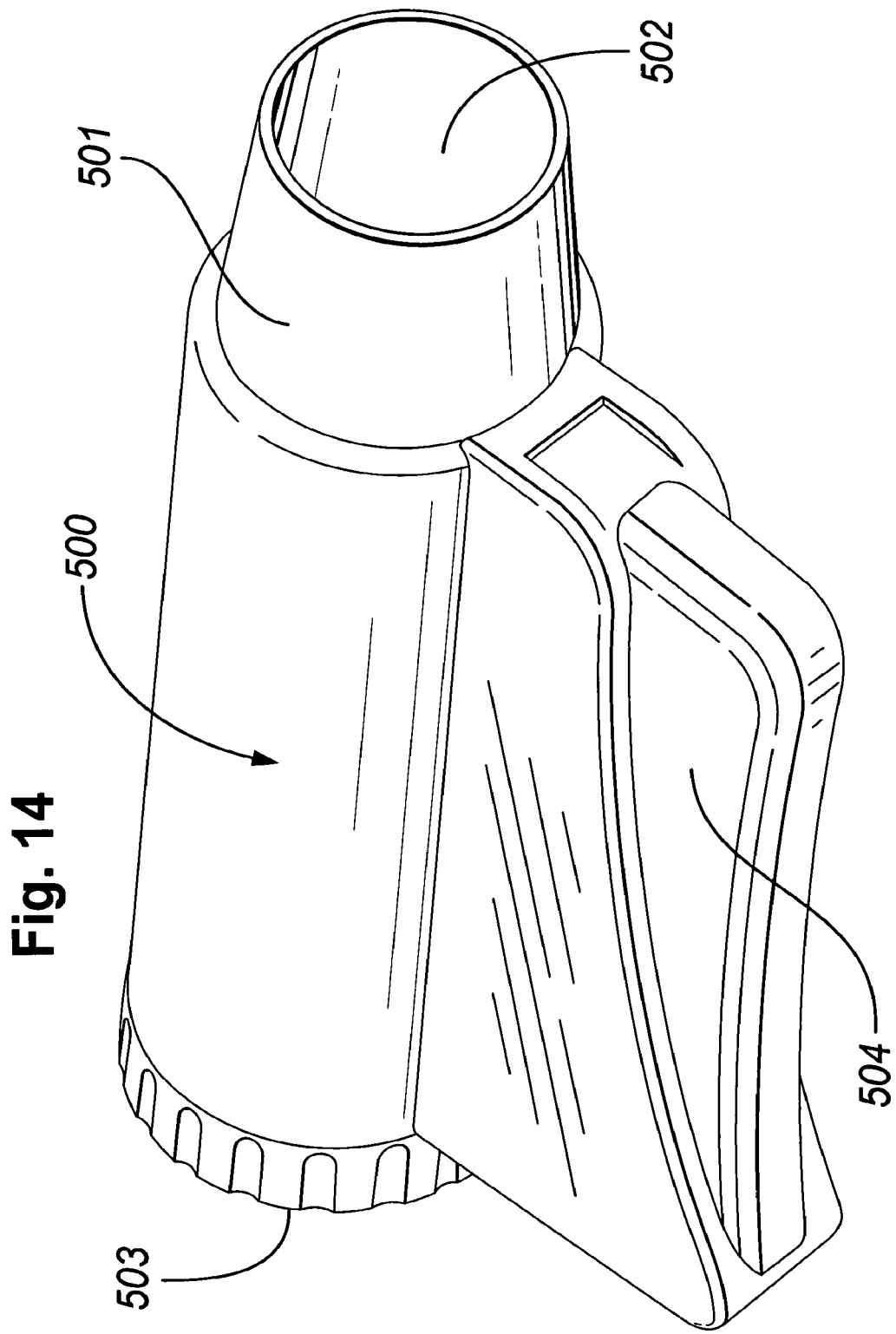
FIG. 14 illustrates manually operable device.

The device illustrated in FIG. 14 comprises a housing 500 incorporating a mouthpiece 501 to a conduit 502 and an inlet 503. A hand squeeze lever 504 is associated with a one-way drive mechanism plus flywheel and gearing (not shown). The lever 504 has radial gear teeth near a pivot end thereof, which teeth engage with a gear on a shaft through a pawl and ratchet or other one-way drive mechanism. A roughly 30 degree angular movement caused by squeezing the lever 504 rotates the shaft about four times. Via the gearing the flywheel is rotated ten times for each shaft rotation and this gives a reasonably steady speed. The flywheel is associated with a disc valve having irregularly spaced voids.

Figure 15:
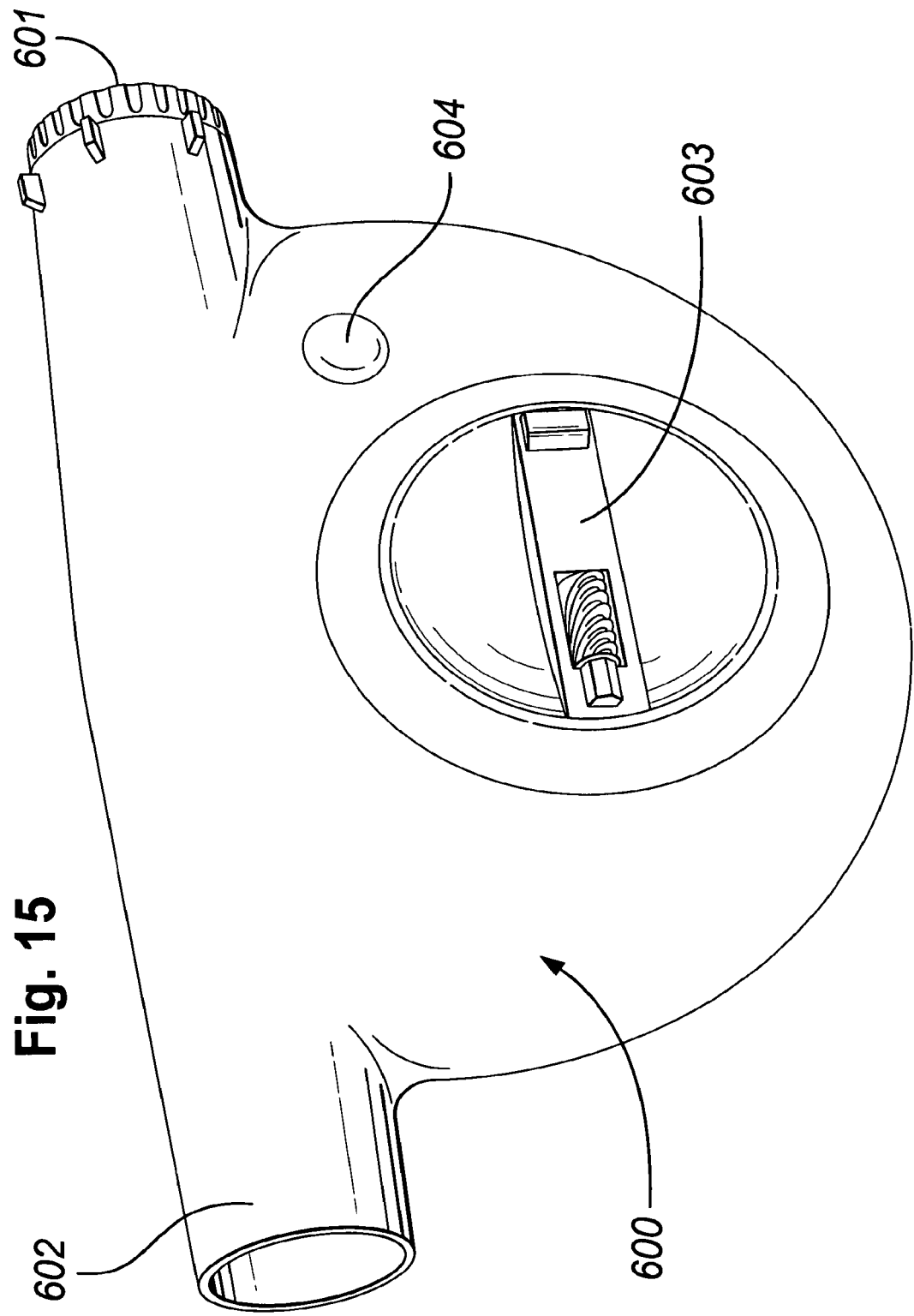
FIG. 15 illustrates a clockwork device.

The device illustrated in FIG. 15 comprises a housing 600 to a conduit having an inlet 601 and a mouthpiece 602. There is shown a stowable wind-up handle 603 and an on-off button 604. Inside the housing and not shown is a wind-up spring, a speed governor in the form of a sprung bob weight and a gear mechanism. The gear mechanism in turn operates a disc valve having irregularly spaced voids. The gear mechanism operates to reduce the valve opening and closing cycle to the order of 20 Hz. The device is openable to enable discs of different perforation pattern to be exchanged therein.

Figure 16:
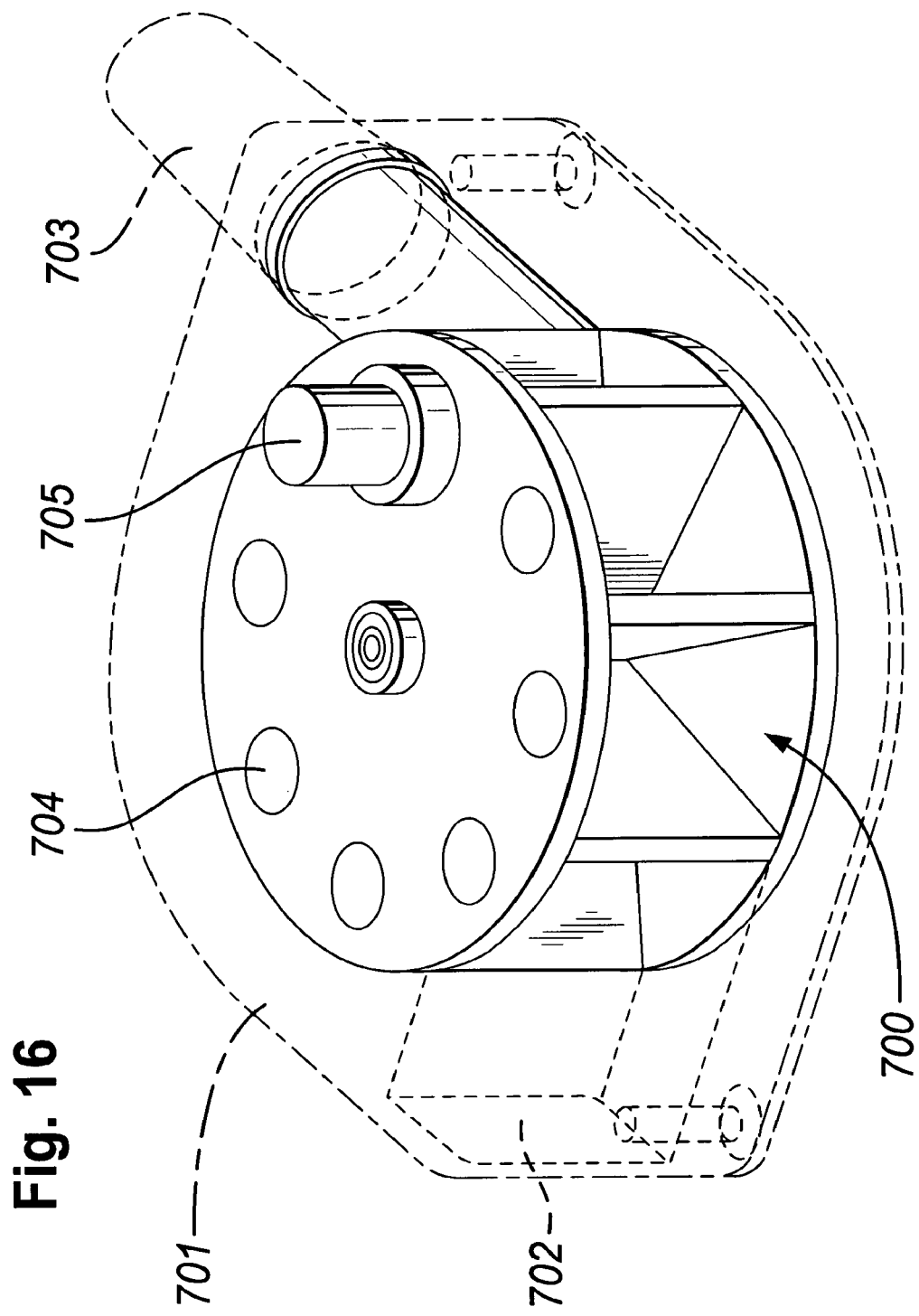
FIG. 16 is a schematic diagram of a device employing magnets.

Shown in FIG. 16 is a rotary vane 700 in a housing 701, the housing having an inlet 702 and a mouthpiece 703. Set around the vane in an irregular array are a plurality of magnets 704 in the form of ferromagnetic discs while in the housing 701 is mounted a co-operating static magnet 705. In this case the co-operation of the rotating magnets 704 on the one hand and the static magnet 705 on the other provides the intermittent resistance to the flow of air in the conduit. This device may be electric motor driven in which case the housing 701 is preferably a head unit detachable from the power unit. Alternatively it may be clockwork or manual lever driven as per the devices herein described with reference to FIGS. 12 and 13.

An important feature of the device illustrated in FIG. 16 however is that it can actually be driven by the respiratory act itself.

The embodiments above described can be compact, with a height of 10 cm, a breadth of 7.5 cm and a thickness of 3.5 cm. They are also robust without being cumbersome so that they are particularly portable and suitable for use by athletes during training.

What is claimed is:

1. A breathing device comprising:
   an air inlet configured to be inhaled through by a user;
   an air outlet configured through which the user can breathe;
   a conduit connecting the air inlet and the air outlet;
   a rotary valve positioned in the conduit so that air entering through the air inlet and inhaled by the user can be interrupted by the rotary valve; and
   means to rotate the rotary valve; and
   means to vary the speed of rotation of the rotary valve to vary the frequency of interruption of the flow of air through the conduit; wherein the frequency of the interruptions to the flow of air is in the range of 5 to 100 Hz.

2. The breathing device of claim 1 and wherein the frequency of interruption of the flow of air can be varied randomly.

3. The breathing device of claim 1 and wherein the frequency of the interruptions to the flow of air is in the range of 10 to 50 Hz.

4. The breathing device of claim 1 and wherein the air outlet incorporates a mouthpiece which is configured to fit over the mouth and/or nose of a user so that a user breathes through the mouthpiece.

5. The breathing device of claim 1 and wherein there is a plurality of valves.

6. The breathing device of claim 5 and wherein the said valves are in series.

7. The breathing device of claim 5 and wherein the said valves are in parallel.

8. The breathing device of claim 5 and wherein one valve is operated at a constant rate and another at a varying rate.

9. The breathing device of claim 1 further comprising a control system which can change the speed of rotation of the valve whilst the device is in use.

10. The breathing device of claim 9 and wherein the control system incorporates a random number generator which controls the speed of rotation of the valves in accordance with the random numbers.

11. The breathing device of claim 1 and wherein the rotary valve comprises;
    a housing containing a fluid flow path with a central axis;
    a plug having a sealing face cooperating with a valve seat in said housing in the closed position to block the fluid flow path; and
    a support shaft arranged to carry said plug and being rotatable on an axis which is normal to and spaced from the axis of said valve seat so that rotation of the said shaft moves said plug relative to said housing.

12. The breathing device of claim 11 and wherein the valve comprises two discs, with each of the discs defining at least one opening therethrough, the discs being positioned in the air flow so that at least one of the discs can rotate relative to the other disc whereby the holes in the two discs are periodically coincident so as to form a continuous air flow passage.

13. The breathing device of claim 1 and wherein the rotary valve comprises a rotary vane, a plurality of spaced apart magnets and a co-operating single magnet.

14. The breathing device of claim 13 and which is arranged to be breath driven.

15. The breathing device of claim 1 and which incorporates a battery.

16. The breathing device of claim 15 and wherein the battery is rechargeable.

17. The breathing device of claim 16 and incorporating means to manually charge the battery.

18. The breathing device of claim 1 and which is powered manually.

19. The breathing device of claim 1 and which is clockwork powered.

20. The breathing device of claim 1 and incorporating data monitoring and data gathering sensors.

21. The breathing device of claim 20 and wherein the sensor measures at least one of pressures, flow rates, adjustment to changes in the rate of interruption of the flow.

22. The breathing device of claim 20 and having a display screen to display data obtained.

23. The breathing device of claim 20 and having means to store the data obtained electronically.

24. The breathing device of claim 20 and having means to transmit data obtained to a remote location.

25. The breathing device of claim 1 and having dimensions no greater than 10 cm*8 cm*4 cm.

26. The breathing device of claim 1 wherein the frequency of interruption of the flow of air through the conduit can be varied whilst the device is in use.

27. A method of training a person or animal comprising interrupting the breathing of the person or animal at a frequency which varies during a training period and wherein controlling of the breathing is carried out by the user breathing in and out through a breathing device as claimed in claim 1.

* * * * *